(12) United States Patent
Price et al.

(10) Patent No.: US 7,533,832 B2
(45) Date of Patent: May 19, 2009

(54) LEG MOUNTED SCENT DISPENSER

(76) Inventors: Roger W. Price, 625 E. McAllister St., Lebanon, IL (US) 62254; Lafareel C. Price, 625 E. McAllister St., Lebanon, IL (US) 62254

(*) Notice: Subject to any disclaimer, the term of this patent is extended or adjusted under 35 U.S.C. 154(b) by 369 days.

(21) Appl. No.: 11/342,199

(22) Filed: Jan. 27, 2006

(65) Prior Publication Data

US 2006/0169793 A1    Aug. 3, 2006

Related U.S. Application Data

(60) Provisional application No. 60/647,450, filed on Jan. 28, 2005.

(51) Int. Cl.
*A62C 15/00* (2006.01)
*B05B 9/08* (2006.01)
(52) U.S. Cl. .................. 239/154; 239/152
(58) Field of Classification Search ......... 239/152–154, 239/302, 337, 338, 344, 354, 373, 361; 222/175, 222/180, 181.2; 248/230.1, 230.8, 231.21, 248/309.1, 311.2, 311.3, 309.2
See application file for complete search history.

(56) References Cited

U.S. PATENT DOCUMENTS

| | | | | | |
|---|---|---|---|---|---|
| 199,193 | A | * | 1/1878 | Stauber et al. | 160/67 |
| 1,248,859 | A | * | 12/1917 | Hitchcock | 239/41 |
| 1,976,340 | A | * | 10/1934 | Gretschel | 239/536 |
| 1,998,734 | A | * | 4/1935 | Parker | 239/152 |
| 3,300,075 | A | * | 1/1967 | Dahl | 215/399 |
| 4,228,933 | A | * | 10/1980 | Elson | 222/400.7 |
| 4,384,675 | A | * | 5/1983 | Jacobs | 239/153 |
| 5,456,036 | A | | 10/1995 | Butz | |
| 6,021,731 | A | * | 2/2000 | French et al. | 114/331 |

* cited by examiner

Primary Examiner—Davis Hwu

(57) ABSTRACT

The leg mounted scent dispenser distributes liquid scent to mask human scent or to deposit a tangle free and consistent scent trail. The dispenser assists hunters in capturing game with weapons and cameras alike. The dispenser includes straps for attaching to a boot and to the lower leg of a person. The boot level strap connects to a canister filled with a scent of the hunter's skillful choice. The canister communicates with a drip valve, or alternatively a pump, that discharges a small portion of scent with each time the boot lands. The person regulates the desired scent flow and walks to a stand or tracks the game. Once at a stand or having taken the game, the hunter turns off the canister and removes the present invention for storage.

1 Claim, 6 Drawing Sheets

LEG MOUNTED SCENT DISPENSER

CROSS-REFERENCE TO RELATED APPLICATIONS

This utility patent application claims the benefit and priority of provisional application Ser. No. 60/647,450, filed Jan. 28, 2005 commonly owned by the same inventors. The above noted application is incorporated herein by reference.

BACKGROUND OF THE INVENTION

The leg mounted scent dispenser relates to hunting equipment in general and more specifically to a dispenser for scent in liquid or powder form.

People have enjoyed wildlife for millennia. Early on, people primarily hunted wildlife and game for sustenance. In recent decades, people have also sought wildlife and game for photography and scientific purposes. From early hunting experience, people learned that game detects human scent and thus avoids people.

Hunters and recently photographers and scientists have also used scent in their quests for game. People have used designed scents to mask human scent and also to entice game towards a hunter, photographer, and the like. Generally, the human masking scent is applied to the body or clothing of a person to counteract the scent and perspiration of a person released when tracking game or waiting for it. When enticing game, scent is applied from a bottle as a hunter or photographer walks through brush and forest. A person inverts the bottle and drips the scent. In doing so, a person keeps one hand occupied thus limiting the person while on rougher terrain or in dense brush. Hunters and photographers have sought a hands free means of dispensing scent.

A unique aspect of the present invention is a canister mounted upon the leg that releases scent with each step. As a person wearing the invention walks across terrain, a trail of scent extends behind him as the person still has both hands free. The scent can mask the person or attract game to the person. When bow hunting or photographing, a person seeks to have the game come to him. After leaving a scent trail while walking, a person reaches a deer stand or blind and waits for the game. With the proper scent and weather conditions, game will approach the waiting person.

DESCRIPTION OF THE PRIOR ART

Scent dispensers and other devices for attracting wildlife and game are known in the prior art. Scent dispensers begin with sticks found by hunters and pressed into service by dipping into a container of scent. The scent coated stick is then dragged behind the hunter. Dispensers then include swabs and sponges for absorbing and then passing scent onto brush and terrain behind a hunter.

The U.S. Pat. No. 5,456,036 to Butz showed a scent dispensing pistol. The pistol has a typical pistol shape with a grip perpendicular to the barrel. The liquid scent is stored in stick like shells. The shells are loaded through the muzzle into the barrel. A triggering mechanism, once pulled by the hunter, then releases a spring loaded plunger that ejects the shell. The shell then fragments upon impact releasing the scent sticks. The hunter then reloads a shell by pulling back on the plunger for the next use of the pistol. Alas, this pistol requires the hunter to dispense each shell with conscious effort. The hunter also has to reload the pistol for each shell. In contrast, the present invention dispenses scent as the hunter walks along without conscious effort and the hunter adds additional scent as the present invention empties from time to time.

The present invention overcomes the limitations of the prior art. That is, the art of the present invention, a leg mounted scent dispenser, provides a canister that drips or sprays scent as the hunter walks along without using the hands of the hunter. Thus, prior art scent dispensing devices do not provide for hands free operation and minimal preparation of the scent for dispersal.

SUMMARY OF THE INVENTION

The leg mounted scent dispenser features a scent distributing and scent covering system designed to mask human scent and to deposit a tangle free and consistent scent trail. The present invention assists hunters in capturing game with weapons and cameras alike. The dispenser includes a strap for attaching to a person's boot and another to the lower leg of a person such as a hunter or photographer. The boot level strap connects to a canister filled with a scent of the hunter's skillful choice. The canister communicates with a drip valve, or alternatively a pump, that discharges a small portion of scent with each step of the boot clad foot. The hunter regulates the desired scent flow and walks to a stand or tracks the game. Once at the stand or having taken the game, the hunter turns off the canister and removes the present invention for storage.

The present invention can be readily used. A hunter places and secures the straps over the boot at ankle height and at calf height, fills the canister with the desired liquid scent, regulates the flow of scent from the canister through the drip valve, and then walks to a stand or tracks the game.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and devices for carrying out the several purposes of the present invention. It is important, therefore, that the claims be regarded as including such equivalent constructions insofar as they do not depart from the spirit and the scope of the present invention.

It is therefore an object of the present invention to provide a new and improved leg mounted scent dispenser that has all of the advantages of the prior art and none of the disadvantages.

It is another object of the present invention to provide a leg mounted scent dispenser that may be easily and efficiently manufactured and marketed.

It is still another object of the present invention to provide a leg mounted scent dispenser that attracts game to the wearer of the dispenser.

It is still another object of the present invention to provide a leg mounted scent dispenser that avoids tangling in brush thus minimizing noise that scares off game.

It is still another object of the present invention to provide a leg mounted scent dispenser that leaves a selected game scent.

It is still another object of the present invention to provide a leg mounted scent dispenser that masks human scent.

It is still another object of the present invention to provide a leg mounted scent dispenser that reduces the drying of scent commonly found when scent is applied to the soles of boots.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The same reference numerals refer to the same parts throughout the various figures.

DETAILED DESCRIPTION OF THE PREFERRED EMBODIMENT

Figure 1:
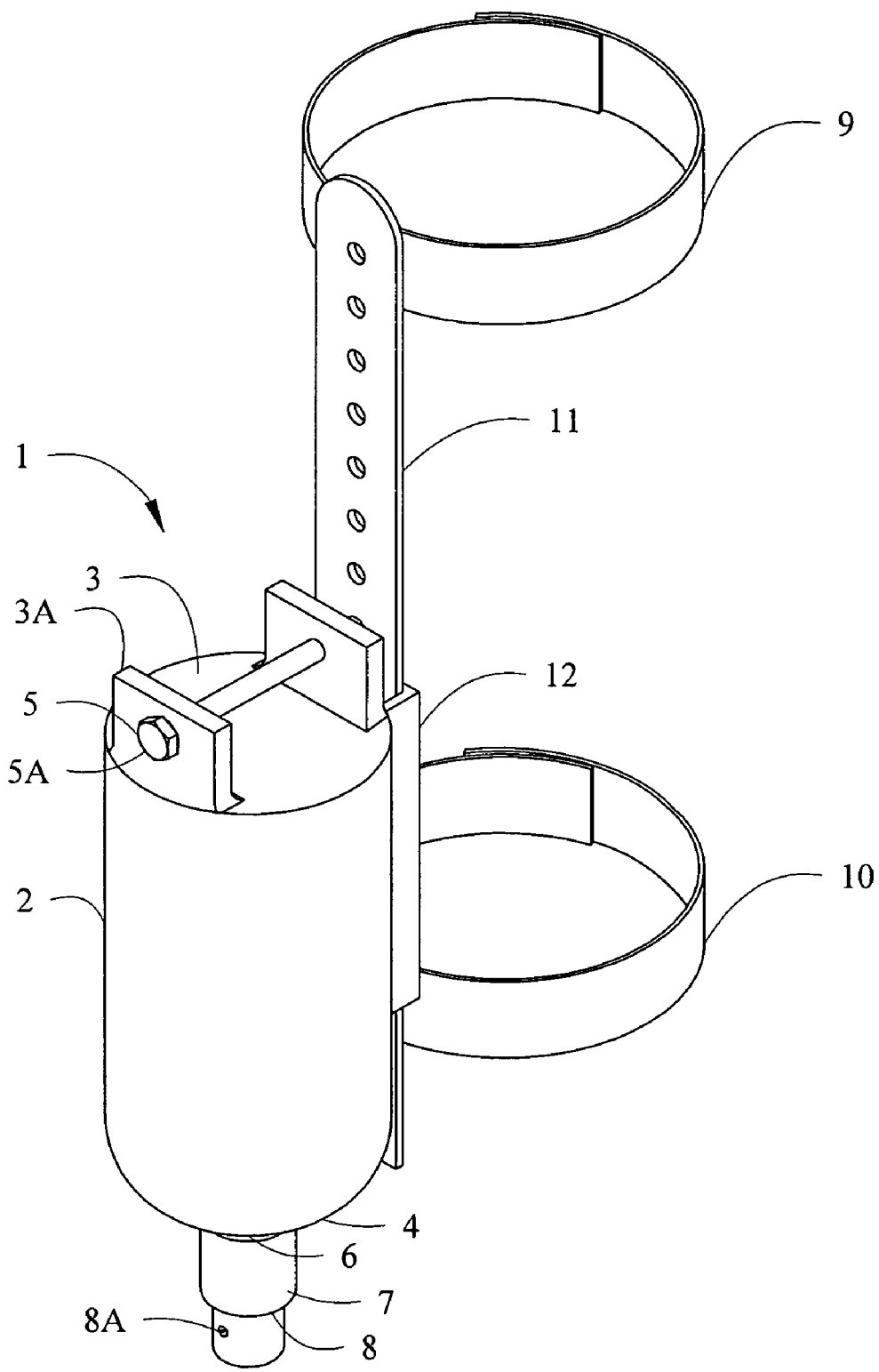
FIG. 1 shows an isometric view of an alternate embodiment of the present is invention.

The present invention 1 overcomes the prior art limitations by providing a canister 2 that dispenses scent with each foot fall as shown in FIG. 1. FIG. 1 shows an alternate embodiment of the invention, particularly in the dispensing mechanism and less so the canister. The canister has a hollow, generally cylindrical shape with rounded corners and sides, a top 3, and an opposite bottom 4. Alternatively, the canister can be a hollow rectangular prismatic shape. Then the canister operates with the longitudinal axis oriented upwards. The top has two spaced apart parallel flanges 3a extending away from the canister. The flanges are generally centered upon the top and have coaxial center holes to admit a means to secure 5 the canister later shown in FIG. 2. The securing means includes a head 5a upon the outside of a flange generally upon the outside of the invention when installed upon the leg of a person.

The bottom is generally flat and has a centered depending neck 6 with a screw cap cover 7. The neck is generally a hollow round cylinder of less diameter than the depth of the canister. The neck has threads wrapped around the circumference and height of the neck to which the screw cap engages. The neck communicates with the interior of the canister to permit the flow of scent out of the canister. Opposite the joining of the neck with the canister, the screw cap closes the neck and restricts flow of scent into an atomizer 8. The atomizer is generally round in cross section and made rugged for contact with the soil when used in the field. The atomizer has an intake in the neck and a port 8a that releases scent generally perpendicular to the longitudinal axis of the canister. The wearer of the present invention can adjust the direction of the port by rotating the atomizer.

Along with the canister, the alternate embodiment includes a calf strap 9 generally above the canister and an ankle strap 10 generally at the same level as the canister. The calf strap and the ankle strap are generally parallel to each other and perpendicular to the longitudinal axis of the canister. A track 11 extends between the calf strap and the ankle strap, perpendicular to both straps. The track has a plurality of holes that cooperate with the securing means 5. The securing means releasably engages the holes so the wearer can adjust the height of the canister.

In use, a wearer of the invention, such as a hunter or wildlife photographer, selects a scent to mask himself or to draw game. The wearer then places the calf strap around his lower leg with the track on the outside of the leg. Placing the ankle strap across a boot or other footwear, the wearer then secures each strap snug upon his leg. The straps can be secured with belt loops and cooperating holes, hook and loop fasteners, buttons, and the like releasable fasteners. The wearer then unscrews the screw cap from the neck and fills the canister with the selected scent. The wearer closes the neck with the screw cap then inverts the canister and secures it upon the track at a chosen height where the head 5a engages a hole in the track. The atomizer has a height where a footfall of the wearer depresses the atomizer to release scent through the port. So as the wearer walks, each step releases scent from the atomizer into the environment to suit the wearer's purpose.

Figure 2:
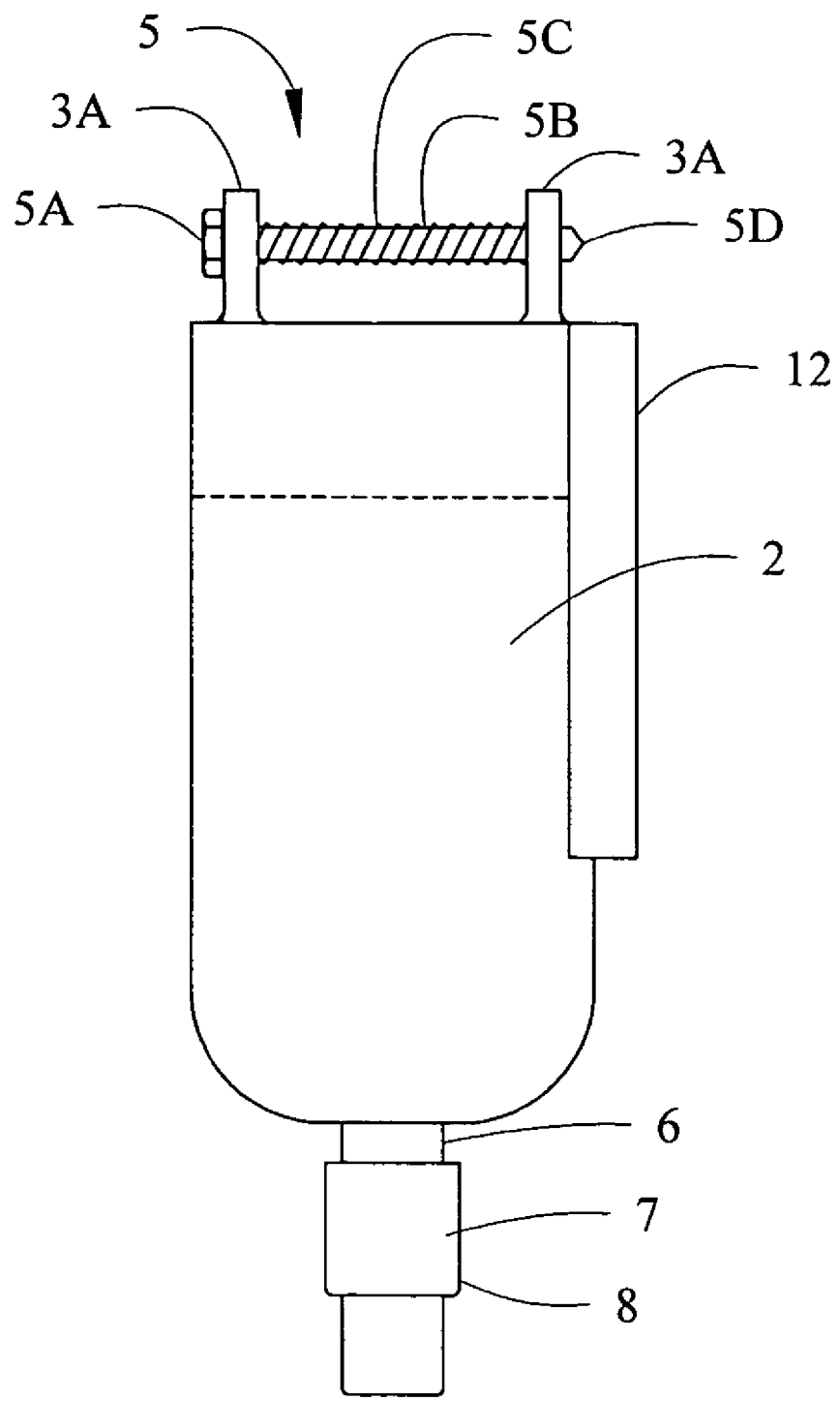
FIG. 2 describes a side view of the canister of the present invention.
Figure 3:
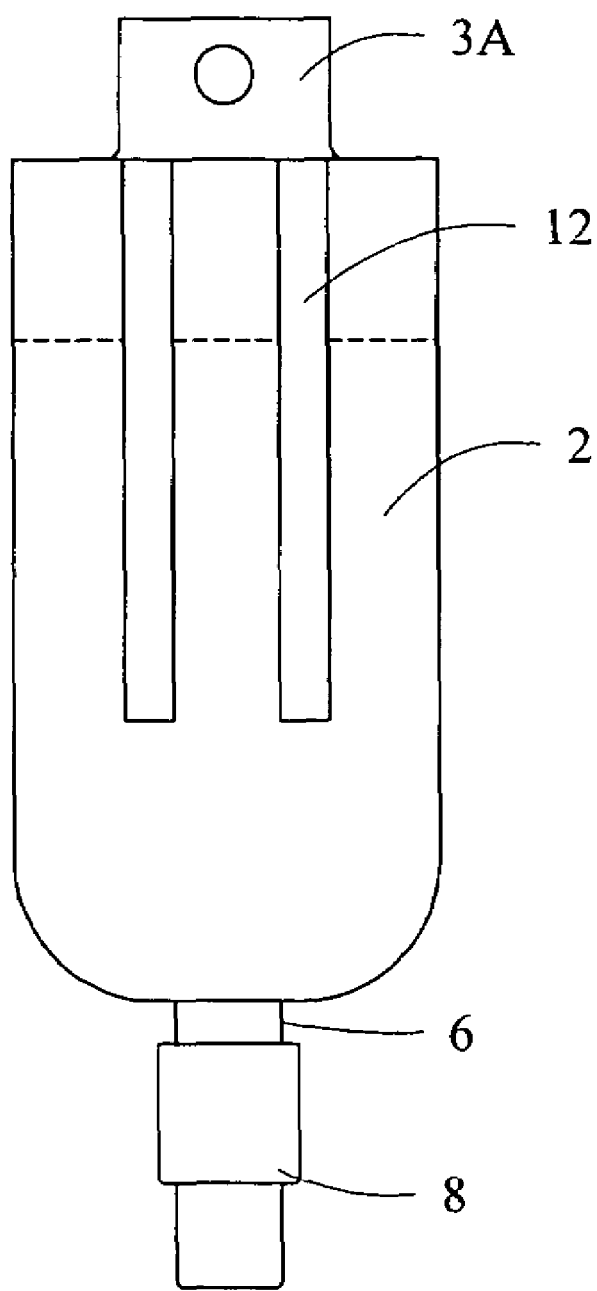
FIG. 3 has a rear view of the canister.

FIG. 2 illustrates where the wearer secures the canister upon the track in the alternate embodiment with the atomizer 8. The track has a plurality of holes, generally in a line along the length of the track. The securing means 5 passes through both flanges 3a at the top 3 of the canister. Preferably, the securing means has a bolt 5b within a spring 5c which is cabined with the flanges 3a. The bolt has a head 5a at one end and an opposite point 5d at the other end. The point engages the holes in the track. The canister also engages the track by two parallel guides 12. Here the guides appear in a side view where their length extends upwards on the canister generally where the canister abuts the leg of the wearer. FIG. 3 shows the rear view of the canister in the alternate embodiment where the guides 12 appear parallel and spaced apart to the width of the track. The guides have a generally L shape turned inwards to grasp the face of the track closer to the leg of the wearer. When a wearer installs or adjusts the canister, the wearer places the guides upon the track then fits the track within the guides. Usually, the wearer slides the canister onto the bottom of the track and raises the canister to the desired position upon the wearer's leg. Once the canister is positioned, the wearer pulls on the head of the securing means which retracts the point. The wearer then releases the head so the spring expands to advance the point into an adjacent hole in the track. The point's connection to a hole and the two guides provide three contacts to secure the canister on the outside of a wearer's leg.

Figure 4:
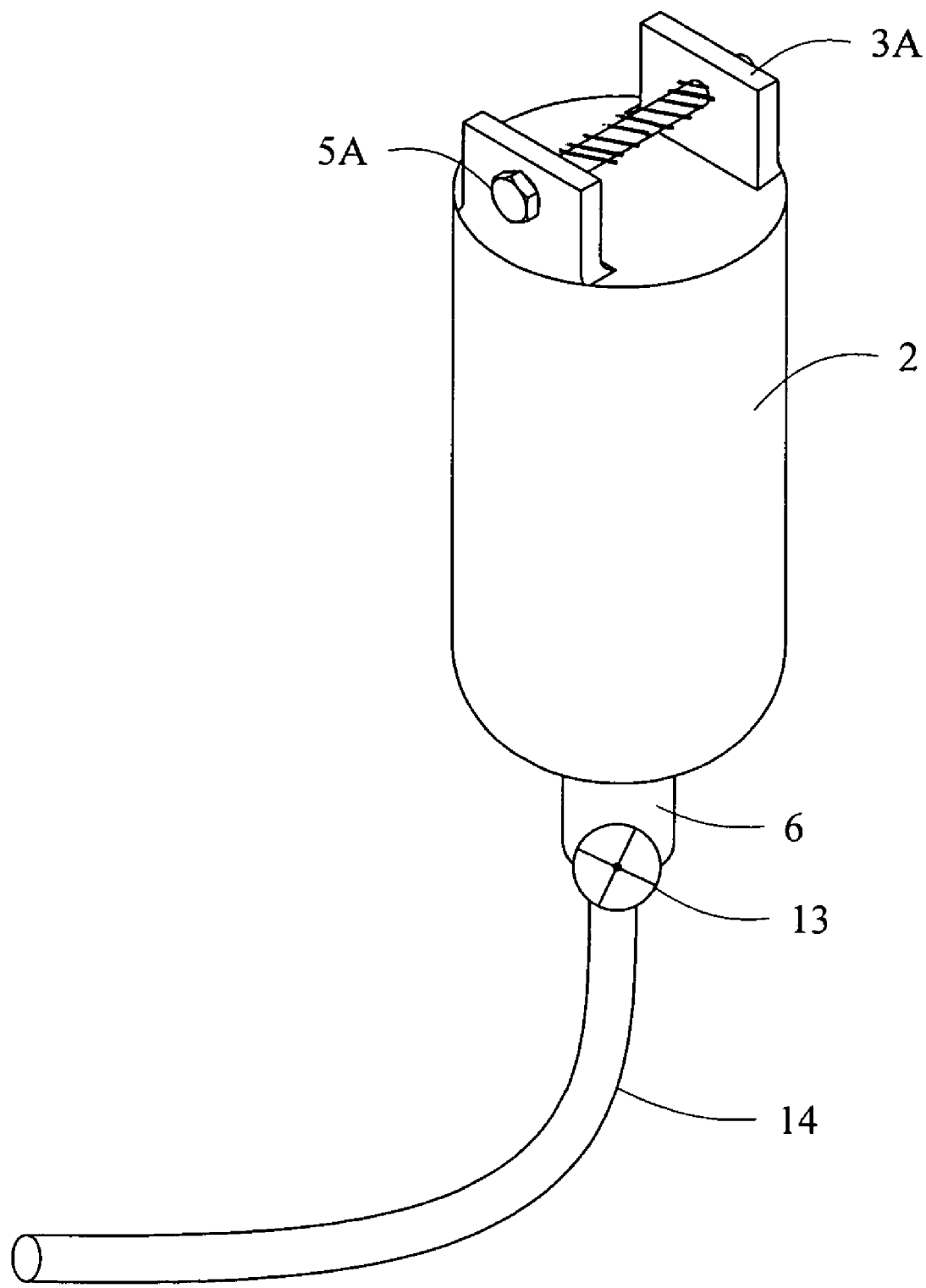
FIG. 4 shows an isometric view of the preferred embodiment of the present invention with a drip valve.

Other means exist to release scent as beginning in FIG. 4. FIG. 4 shows the canister as previously described including the securing means, this form of the canister though is the preferred embodiment. The canister has a neck that communicates scent from the bottom of the canister for release. Instead of an atomizer releasing at each footfall, a wearer may desire release of scent continuously during movement. The neck in the preferred embodiment includes a drip valve 13. The drip valve turns to regulate the flow of scent, generally as a liquid, out of the canister into a tube 14. Turning of the drip valve allows the wearer to select the desired scent flow while the tube drags along behind the wearer when walking. The tube is generally a flexible plastic tube of sufficient wall thickness for rugged field use. As before, the canister mounts to a track and the wearer selects the height of the canister upon his leg. The drip tube does permit more flexibility in canister height than the atomizer.

Figure 5:
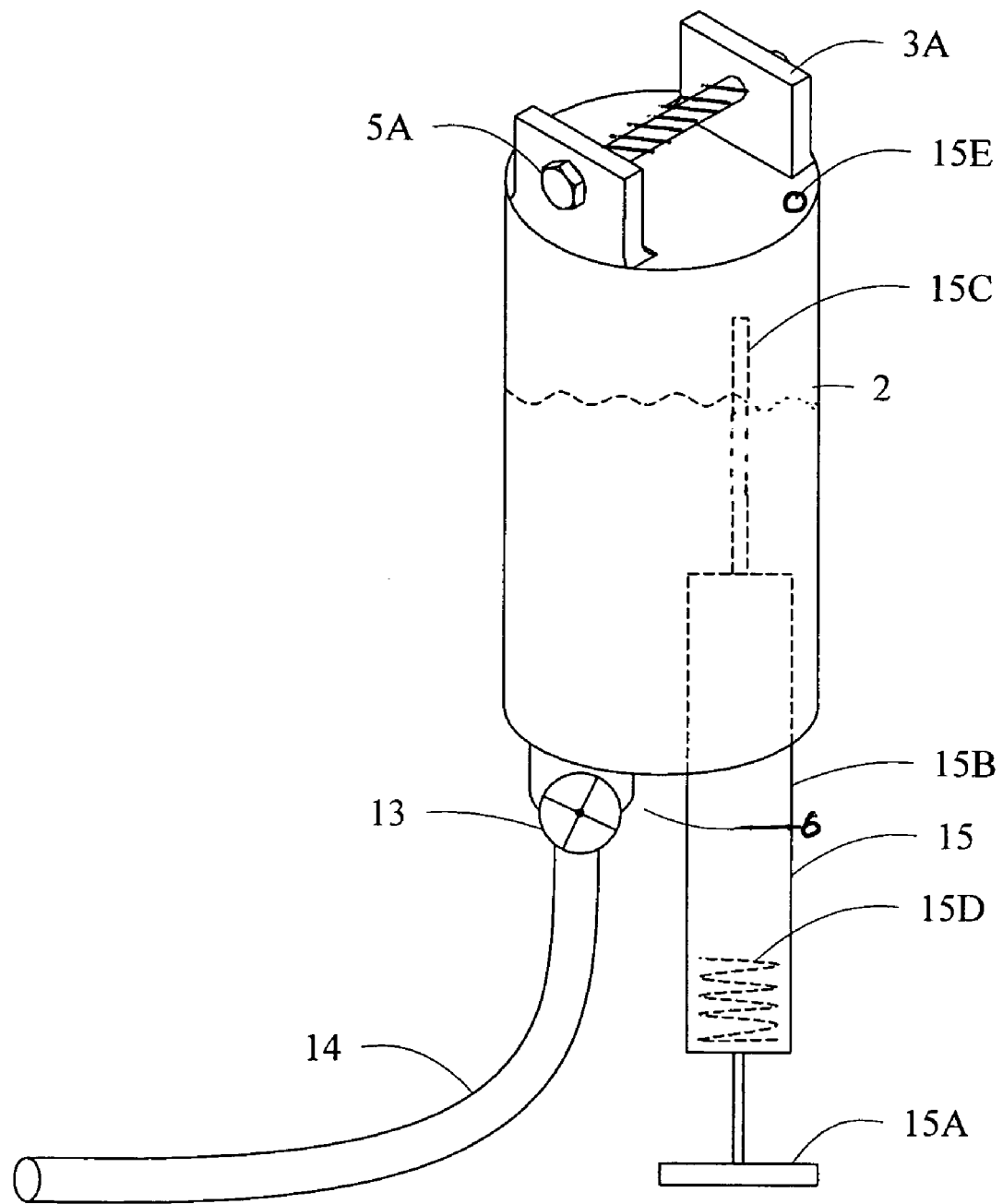
FIG. 5 shows an isometric view of the preferred embodiment of the present invention with a foot pump; and, FIG. 6 shows an isometric view of an alternate embodiment of the present invention installed upon a belt at hip height of a person.

Blending the alternate embodiment of FIG. 1 with the preferred embodiment in FIG. 2, FIG. 5 shows an alternate embodiment that pressurizes dispensing of scent from the canister. As before, the canister has a top from which flanges extend that support the securing means. Opposite the top, the canister has a generally flat bottom from which a neck extends to a drip valve 13. The drip valve can be adjusted to regulate the release of scent into the drip tube 14. The bottom also has a opening through which inserts a foot pump 15. The foot pump has a plunger 15a that extends to ground level when this embodiment is worn. The plunger extends through the pump body within a spring 15d, beyond an intake 15b and into the interior of the canister. The pump body ends in a nozzle 15c generally located above the maximum fill line of the canister. As the wearer walks, the plunger passes back and forth past the intake to add air into the pump body. The plunger then presses the air from the pump body through the nozzle and into the canister. The canister then becomes pressurized and releases scent strongly through the drip valve. This embodiment is useful for wearers who seek to spread scent a distance away from their footprints. However, to counteract excessive pressure buildup, the canister has a relief valve 15E in the top to vent excessive pressure that would otherwise blow the seals of the foot pump and drip valve.

Figure 6:
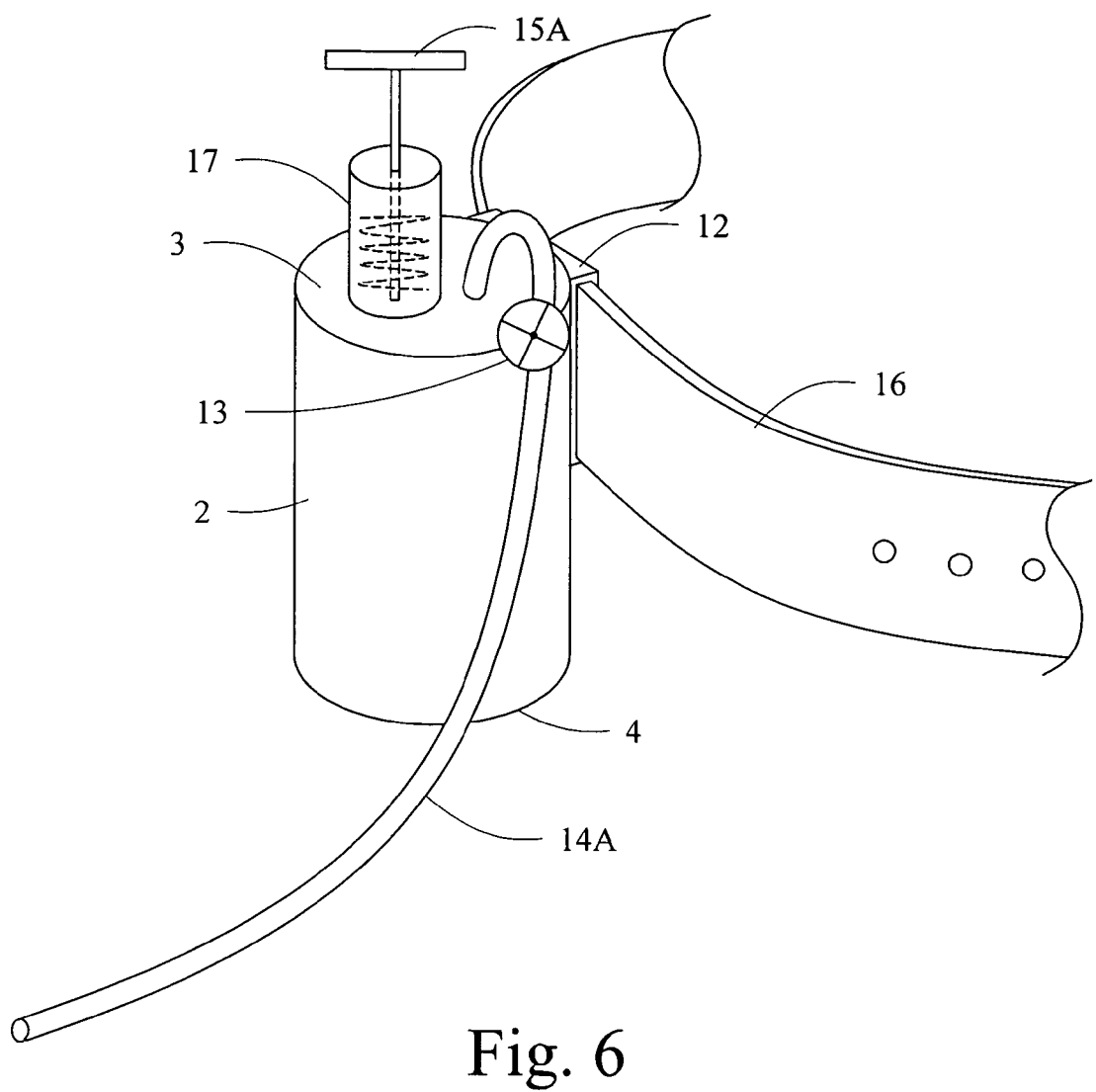

Some wearers seek further control over dispensing scent. FIG. 6 shows an alternate embodiment where the canister 2 is mounted upon a belt 16 by a belt clip 12a. The belt clip extends from the rear of the canister in place of the guides 12. In this embodiment the canister has a generally round or cylindrical shape with rounded corners and sides as before along with a flat bottom. The top is generally flat with two openings therethrough. A pump 17 extends from one opening into the canister. The pump has a spring loaded plunger 15a that the wearer depresses to pressurize the scent inside the canister. The pump, similar to the foot pump, has an intake hole past which the plunger passes. When the scent pressurizes, the scent escapes through the second opening into the tube 14a. The tube extends from the top of the canister to ground level for dispensing scent as the wearer walks along. The wearer adjusts dispensing of the scent through a drip valve 13 adjacent to the top of the canister in communication with the tube. In using this embodiment, the wearer presses the plunger repeatedly to pressurize the air and scent liquid inside the canister. Desiring to dispense scent, the wearer opens the drip valve so that scent flows through the tube back to ground level as the wearer walks. This alternate embodiment may also be hung upon a tree or other fixed object to dispense scent in the vicinity thereof.

From the aforementioned description, a leg mounted scent dispenser has been described. The leg mounted scent dispenser is uniquely capable of releasing scent with each footfall of a hunter or other outdoorsman. The leg mounted scent dispenser and its various components may be manufactured from many materials, including but not limited to polymers, polyvinyl chloride, high density polyethylene, polypropylene, Plexi-glass®, fiberglass, rubber, latex, nylon, ferrous and non-ferrous metals, their alloys, and composites.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

We claim:

1. A device for dispensing scent adapted to be secured to a person comprising:
   a hollow canister having a longitudinal axis oriented upright, a bottom and an opposite top, at least one side between said bottom and said top;
   a releasable mechanism upon said side, said releasable mechanism adapting to secure said device upon a person;
   a dispenser upon said bottom of said canister;
   said canister having at least one integral flange extending upwards from said top, said flange including at least one hole therethrough and at least one guide extending upright upon said side generally parallel to said flange;
   said releasable mechanism including a bolt, said bolt having a slender elongated shape with a point and an opposite head and a spring coaxial and surrounding said bolt;
   two spaced apart parallel straps joined by a track tangential and generally perpendicular to said straps, said track having two parallel edges and holes between the edges;
   said guide adapted to travel along the track; and,
   said bolt passing through said hole in said flange, and said point entering a hole upon said track.

* * * * *